United States Patent
Aferzon et al.

(10) Patent No.: US 9,463,096 B2
(45) Date of Patent: *Oct. 11, 2016

(54) APPARATUS FOR ANTERIOR INTERVERTEBRAL SPINAL FIXATION AND FUSION

(71) Applicant: International Spinal Innovations LLC, West Hartford, CT (US)

(72) Inventors: Joseph Aferzon, Avon, CT (US); Joshua Aferzon, Avon, CT (US)

(73) Assignee: International Spinal Innovations LLC, West Hartford, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 14/719,895

(22) Filed: May 22, 2015

(65) Prior Publication Data

US 2015/0265416 A1 Sep. 24, 2015

Related U.S. Application Data

(60) Division of application No. 13/335,382, filed on Dec. 5, 2011, now Pat. No. 9,039,770, which is a continuation of application No. 12/567,691, filed on Sep. 25, 2009, now Pat. No. 8,070,819, which is a division of application No. 11/321,936, filed on Dec. 29, 2005, now Pat. No. 7,594,932.

(51) Int. Cl.
*A61F 2/44* (2006.01)
*A61F 2/46* (2006.01)
*A61F 2/30* (2006.01)

(52) U.S. Cl.
CPC ............. *A61F 2/4425* (2013.01); *A61F 2/447* (2013.01); *A61F 2/4611* (2013.01); *A61F 2/446* (2013.01); *A61F 2002/30365* (2013.01); *A61F 2002/30579* (2013.01); *A61F 2002/30841* (2013.01); *A61F 2002/30845* (2013.01); *A61F 2002/4445* (2013.01); *A61F 2002/4475* (2013.01); *A61F 2002/4627* (2013.01); *A61F 2220/0016* (2013.01); *A61F 2220/0033* (2013.01)

(58) Field of Classification Search
CPC .................... A61F 2/447; A61F 2002/30579; A61F 2002/30845
See application file for complete search history.

(56) References Cited

U.S. PATENT DOCUMENTS 2,864,421 A * 12/1958 Schmidt ..................... 83/665
5,522,441 A * 6/1996 Anselm et al. ................. 142/41
6,012,372 A * 1/2000 Laster et al. .................... 83/665
6,159,211 A * 12/2000 Boriani et al. ................ 606/279
6,227,093 B1 * 5/2001 Rensky, Jr. ...................... 83/563
6,302,914 B1 * 10/2001 Michelson ................. 623/17.16

(Continued)

*Primary Examiner* — Ellen C Hammond
(74) *Attorney, Agent, or Firm* — Dinsmore & Shohl LLP

(57) ABSTRACT

A fixation device includes a housing, first and second shafts, first blade, and second blade. The housing includes a leading surface and trailing surface. The first and second shafts run from the leading surface to the trailing surface. The first blade has a first extension with a sharp edge extending from the first shaft in a first orientation about the first shaft. The second blade has a second extension with a sharp edge extending from the second shaft in a second orientation about the second shaft. The first blade is rotatable according to the first orientation and the second blade is rotatable according to the second orientation, such that the first extension and the second extension are enabled to break an endplate of a vertebra, hook into the vertebra, and rigidly secure the vertebra to the device to prevent separation of the vertebra from the device during spinal motion.

16 Claims, 18 Drawing Sheets

(56) References Cited

U.S. PATENT DOCUMENTS

| | | | |
|---|---|---|---|
| 6,443,990 B1 * | 9/2002 | Aebi et al. | 623/17.16 |
| 6,447,544 B1 * | 9/2002 | Michelson | 623/17.16 |
| 6,447,547 B1 * | 9/2002 | Michelson | 623/17.16 |
| 6,527,803 B1 * | 3/2003 | Crozet et al. | 623/17.11 |
| 6,558,424 B2 * | 5/2003 | Thalgott | 623/17.16 |
| 6,770,096 B2 * | 8/2004 | Bolger et al. | 623/17.16 |
| 6,824,564 B2 * | 11/2004 | Crozet | 623/17.11 |
| 7,238,203 B2 * | 7/2007 | Bagga et al. | 623/17.11 |
| 7,594,932 B2 * | 9/2009 | Aferzon et al. | 623/17.16 |
| 8,070,819 B2 * | 12/2011 | Aferzon et al. | 623/17.16 |
| 9,039,770 B2 * | 5/2015 | Aferzon et al. | 623/17.16 |
| 2002/0143401 A1 * | 10/2002 | Michelson | 623/17.16 |
| 2003/0004576 A1 * | 1/2003 | Thalgott | 623/17.16 |
| 2003/0187436 A1 * | 10/2003 | Bolger et al. | 606/61 |
| 2004/0138752 A1 * | 7/2004 | Michelson | 623/17.11 |
| 2007/0270968 A1 * | 11/2007 | Baynham et al. | 623/17.11 |
| 2008/0255666 A1 * | 10/2008 | Fisher et al. | 623/17.16 |

\* cited by examiner

APPARATUS FOR ANTERIOR INTERVERTEBRAL SPINAL FIXATION AND FUSION

CROSS REFERENCE TO RELATED APPLICATIONS

The present application is a divisional of U.S. patent application Ser. No. 13/335,382, filed Dec. 5, 2011, which is a continuation of U.S. patent application Ser. No. 12/567,691, filed on Sep. 25, 2009, which is a divisional of U.S. patent application Ser. No. 11/321,936, filed on Dec. 29, 2005, the contents of which are incorporated herein by reference in their entirety.

FIELD OF INVENTION

This invention relates to a spinal fusion device. More specifically, the present invention relates to an implant and fixation device used to reconstruct spinal disk space and facilitate fusion across the spinal disk space.

BACKGROUND

Articulations between bony vertebrae of a human spine frequently deteriorate with age or trauma and become a source of pain. A spinal disk is one of these articulations and with the aging process it loses its normal consistency and volume and collapses allowing for abnormally painful motion within the anterior spinal column The spinal disk is a complex cylindrical weight-bearing fibrous structure with a non-compressible viscous center. The spinal disk articulates with bony vertebrae above and below through a large surface area circular interface known as an endplate. The endplate is a thin (1-3 mm) approximately round 2-4 cm in diameter plate of dense bone and cartilage accounting for a majority of the weight-bearing capacity.

Surgical treatment of disk disorders frequently requires elimination of movement across an abnormal spinal disk. This is accomplished by allowing bone to grow between adjacent vertebrae and through a disk space of the abnormal spinal disk. It is desirable to reconstruct the disk space to its prior normal height by opening the space previously occupied by the removed spinal disk while retaining normal curvature of the spine determined by the differential height between the front and the back of the spinal disk (FIG. 3). This is commonly achieved by using inserts or implants which open the disk space and which allow for growth of the bridging bone. The ultimate effectiveness of an implant is based on the following factors: (i) ability to reconstruct and maintain a normal configuration of a vertebral column; (ii) ease of insertion; (iii) facilitation of bony fusion; and (iv) restriction of movement across the disk space Implants utilized in fusion of a human spine and delivered in a straight trajectory through the front of the spine and into the disk space are well known to those skilled in the art. They vary in shape but possess similar characteristics with upper and lower surfaces conforming to a shape of vertebral endplates and a vertical design aiming to open or reconstruct the collapsed disk space. These implants are sufficiently porous or hollow to allow bone to grow through the implants and bridge two vertebrae referred to as bone fusion. These implants perform well with vertical loading of the spine or in flexion. However, these implants are not able to restrict the movement between two vertebrae when vertebrae are pulled apart or are in extension and lateral bending. Further, these implants provide negligible restriction during sliding motion (translation) and rotation.

Devices that cut into or have protrusions directed into or through the endplate, are also known in the related art. These protrusions penetrate the endplate and potentially create channels for a bone growth, yet the protrusions do not alter structural properties of the endplate. The protrusions reduce the risk of extrusion of the implant out of the disk space. These protrusions negligibly restrict translation or sliding motion but they do not restrict extension and lateral bending. This necessitates additional fixation (immobilization) usually consisting of posterior pedicle screws.

There would be a substantial benefit in an anterior fixation device which would on its own rigidly fixate the spine in all direction of motion.

SUMMARY OF THE INVENTION

A device for reconstruction, fixation and bone fusion through anterior approach to the human spine. This device enables rigid fixation in all planes of motion including extension of the spine, it possesses structural characteristics necessary to reconstruct and maintain disk height, it provides space for bone grafting material and produces a plurality of extension of the spine, it possesses structural characteristics necessary to reconstruct and maintain disk height, it provides space for bone grafting material and produces a plurality of perforations through endplates above and below to enhance bony fusion.

In some aspects or embodiments, there is provided a fixation device. The fixation device includes a housing, first and second shafts, at least one first blade, and at least one second blade. The housing includes at least a leading surface and a trailing surface. The first and second shafts run from the leading surface to the trailing surface of the housing.

The at least one first blade has at least one first cutting extension with a sharp leading edge extending from the first shaft in a first orientation about the first shaft, while the at least one second blade has at least one second cutting extension with a sharp leading edge extending from the second shaft in a second orientation about the second shaft. The second orientation is opposite to the first orientation.

The at least one first blade is rotatable in a direction according to the first orientation and the at least one second blade is rotatable in an opposite direction according to the second orientation, such that the at least one first cutting extension of the at least one first blade and the at least one second cutting extension of the at least one second blade are enabled to break an endplate of a vertebra, hook into the vertebra, and rigidly secure the vertebra to the fixation device to prevent separation of the vertebra from the fixation device during spinal motion.

In some aspects or embodiments, the at least one first blade can include a first set of opposing cutting extensions with sharp leading edges that are enabled to break endplates of adjacent vertebrae, hook into the adjacent vertebrae, and rigidly secure the adjacent vertebrae in relation to each other and to the fixation device to prevent separation of the vertebrae from the fixation device during spinal motion. Moreover, the at least one second blade can include a second set of opposing cutting extensions with sharp leading edges that are enabled to break the endplates of adjacent vertebrae, hook into the adjacent vertebrae, and rigidly secure the adjacent vertebrae in relation to each other and to the fixation device to prevent separation of the vertebrae from the fixation device during spinal motion.

In some aspects or embodiments, the at least one first blade can rotate in a clockwise direction according to the first orientation, while second blade can rotate in a counterclockwise direction according to the second orientation.

In some aspects or embodiments, the at least one first blade and the at least second blade are imbricated between each other. Moreover, the at least one first blade and the at least second blade can be rotated individually or as a group. Further, the at least one first blade and the at least second blade can vary in size.

In some aspects or embodiments, the at least one first blade and the at least second blade can include portions that are configured to expand a disk space between adjacent vertebrae. Moreover, the portions can be configured to provide weight-bearing support to the adjacent vertebrae.

In some aspects or embodiments, the first and second shafts can serve as axis of rotation to the at least one first blade and the at least second blade. The first and second shafts can be fixed in relation to each other. Moreover, the first and second shafts can move away from each other when the housing is expanded at least in part in vertical and horizontal directions.

In some aspects or embodiments, the first and second shafts can run perpendicularly to the leading surface of the housing. Moreover, the housing can have a configuration of a box, a cylinder, or another geometric shape, wherein the configuration includes a height of the deep surface that is smaller than a height of the trailing surface.

In some aspects or embodiments, the housing can include at least one material selected from metal, plastic ceramic, graphite, coral, and human bone product. The housing can be formed at least in part from a porous material. Moreover, the housing can be absorbable.

DETAILED DESCRIPTION

An implant device for reconstruction, fixation and bone fusion of bone vertebrae through an anterior approach to the human spine. This implant device enables rigid fixation in all planes of motion including extension of the spine, it possesses structural characteristics necessary to reconstruct and maintain disk height, it provides space for bone grafting material and produces a plurality of perforations through endplates above and below to enhance bony fusion.

The implant device consists of the outer structure or shell which is designed to conform to the disk space, provide openings for bony ingrowths and maintain the disk height by providing adequate structural strength and sufficient weight bearing surface. The shell or housing contains a shaft (10) which runs through its central axis from the back (9) to the front (8) and is fixed to the shell (FIG. 7).

Figure 12:
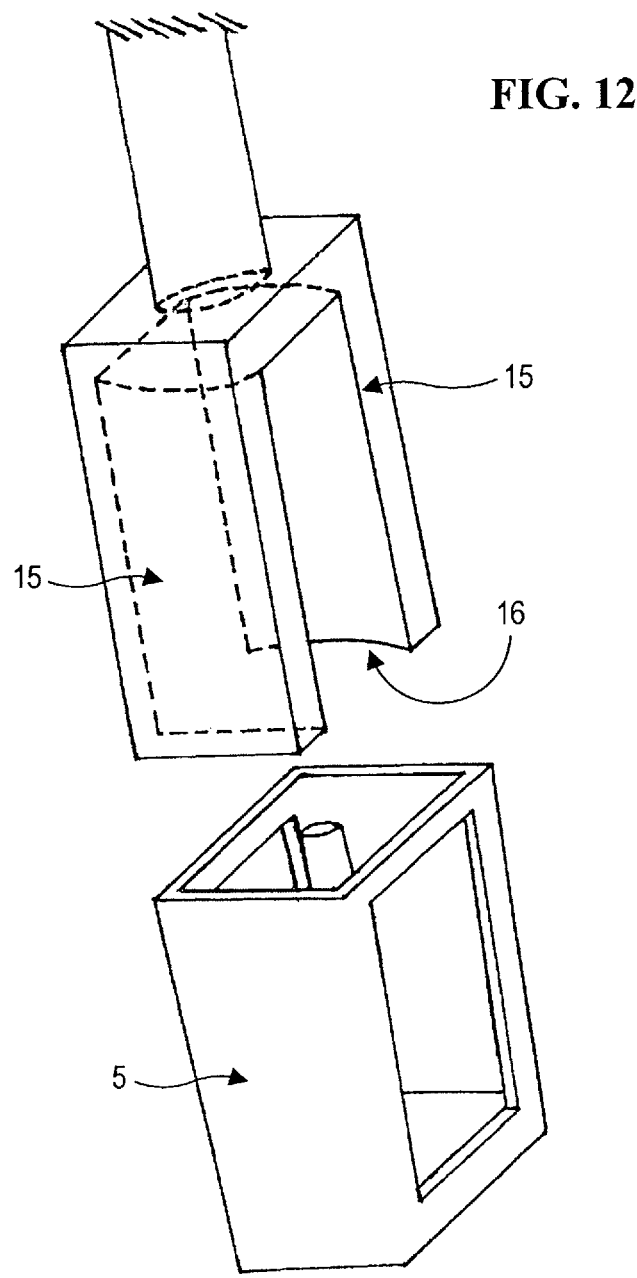
FIG. 12 illustrates a preferred embodiment of an insertion instrument for the housing. Prongs (15) fit inside the lateral walls (5) of the housing but clear the central opening (16) occupied by the blades (14).
Figure 13:
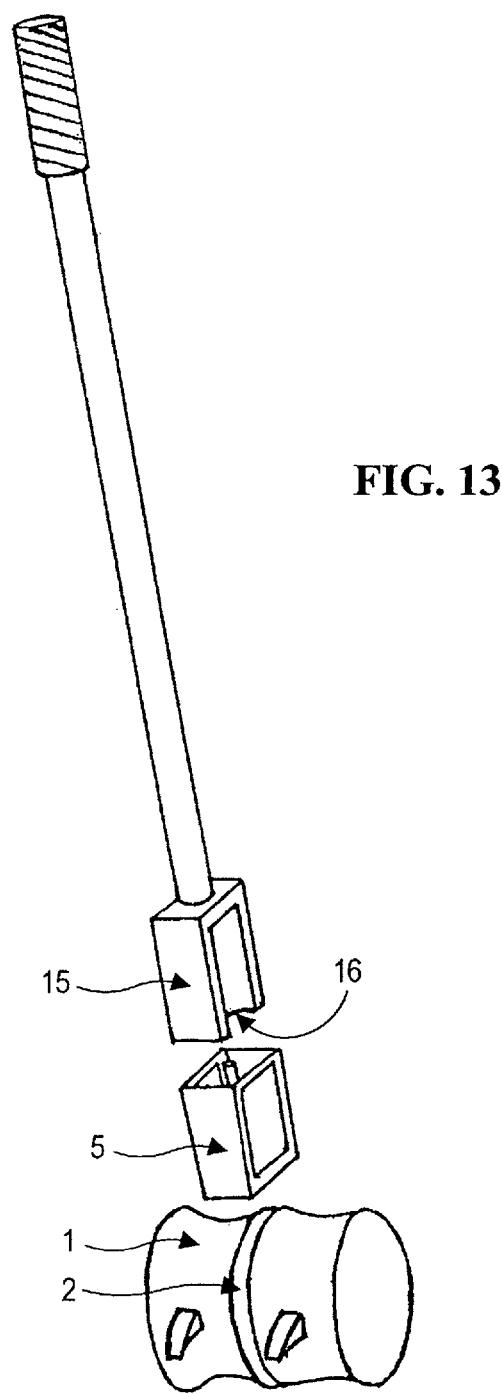
FIG. 13 illustrates a preferred method of placing the housing into a collapsed disk space (2) between vertebrae (1).
Figure 14:
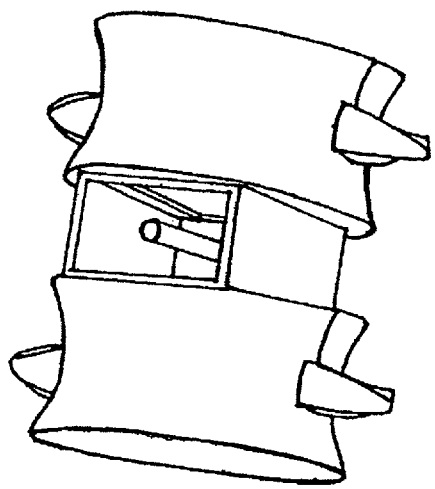
FIG. 14 illustrates a housing inside an expanded disk space (2).

In the preferred embodiment the shell is impacted into the disk space (FIG. 14) using the shell introducer (FIG. 13). The shell introducer includes prongs (15) that fit inside the sides (5) of the shell but is open (16) in the center to allow for blades (FIG. 12).

Figure 11:
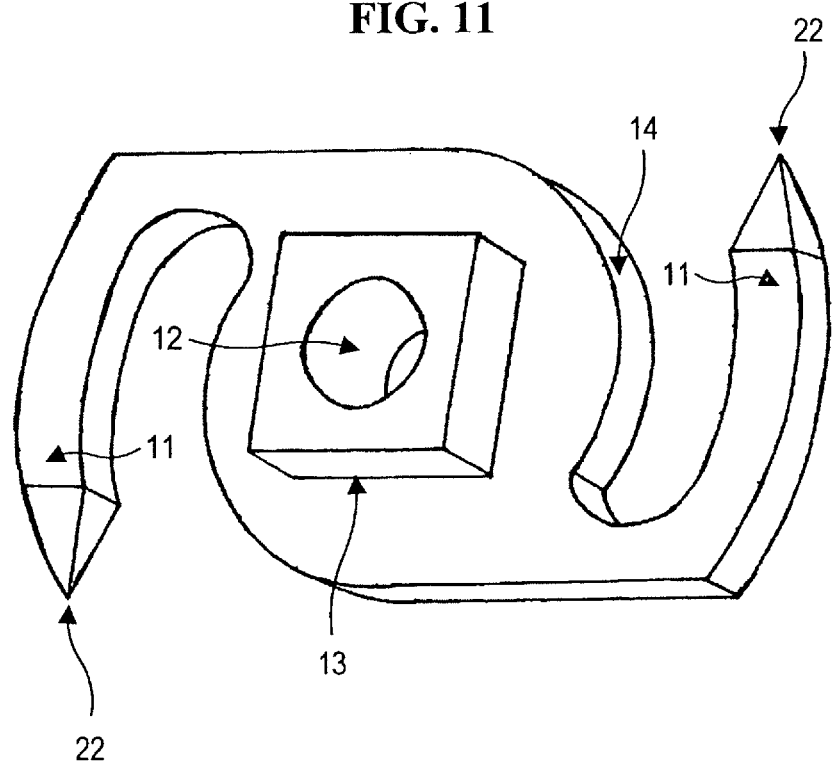
FIG. 11 illustrates a perspective view of the counterclockwise blade (14).
Figure 15:
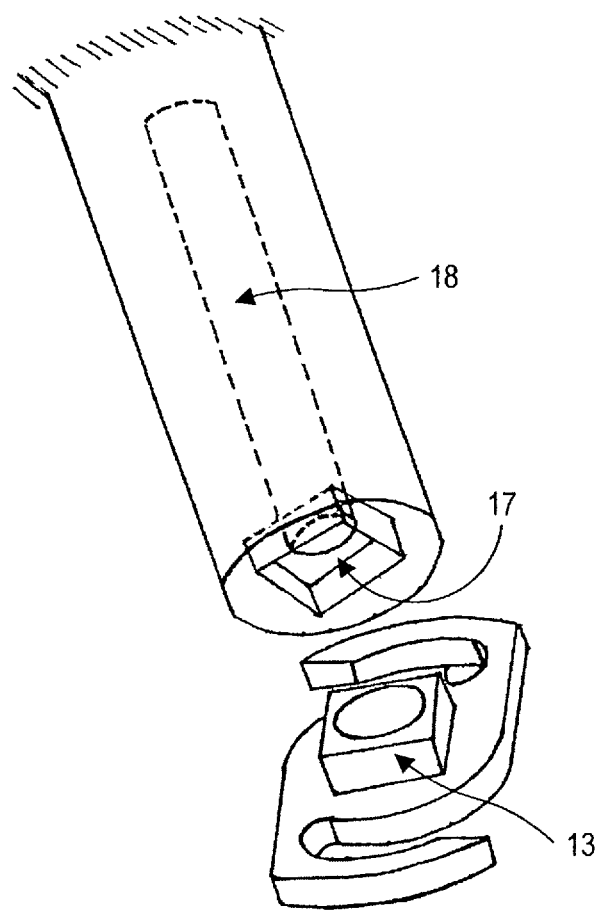
FIG. 15 illustrates a preferred embodiment of a blade introducer having a receptacle (17) for the control nut (13) and central opening (18) for the shaft (10).
Figure 16:
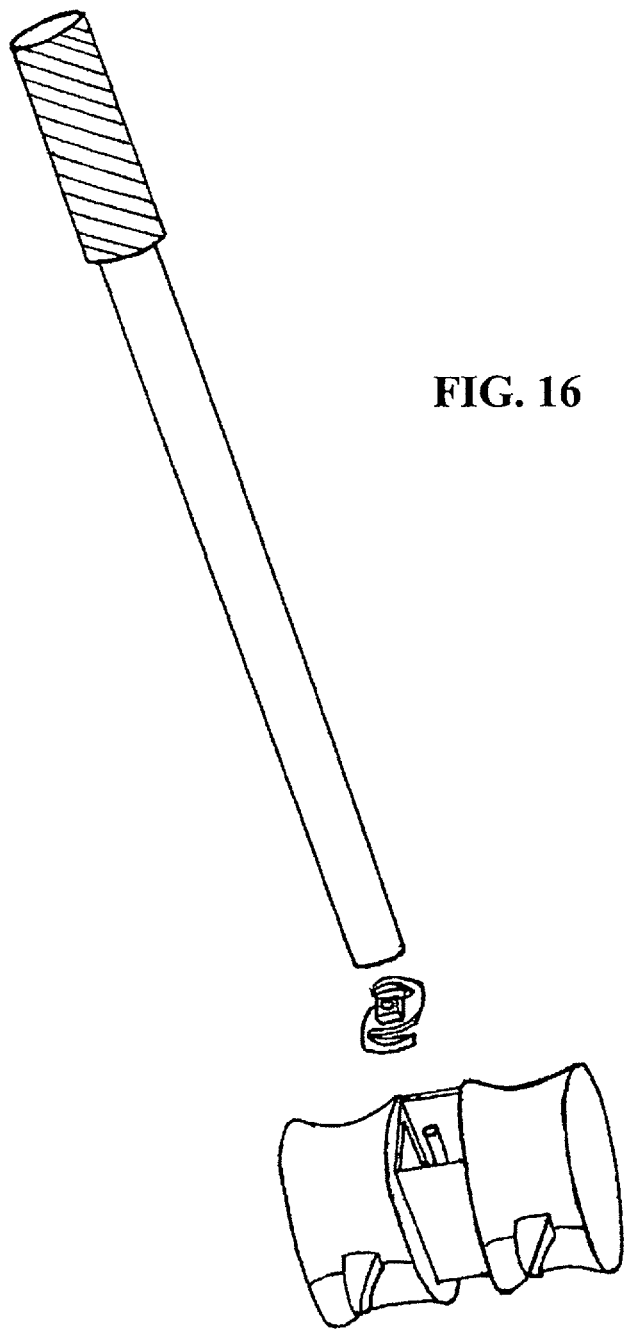
FIG. 16 illustrates a blade (14) of FIG. 8 introduced horizontally into the housing of FIG. 7 using the blade introducer of FIG. 15.
Figure 17:
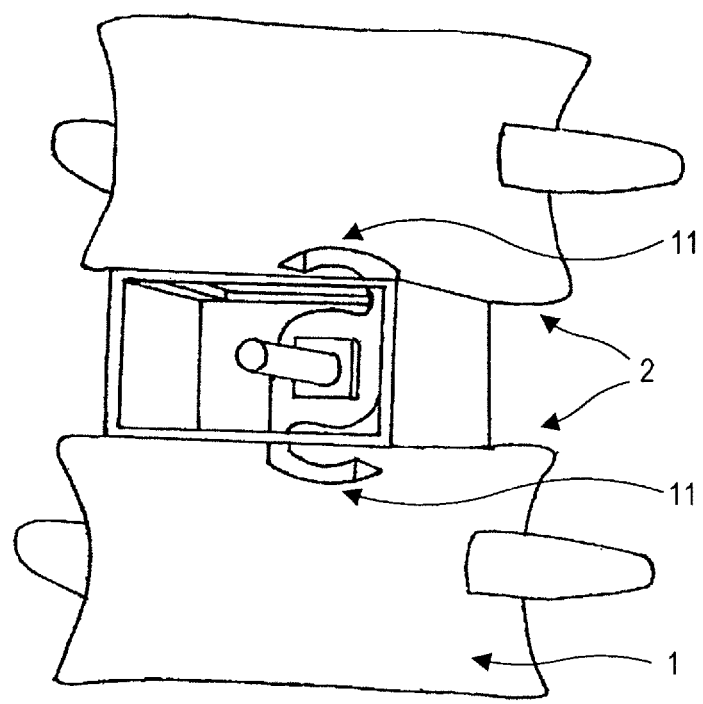
FIG. 17 illustrates a blade (14) rotated vertically with cutting extensions (11) piercing vertebral endplates and hooking into vertebrae (1).

Once the shell is placed in a correct position between vertebrae (1), individual blades (FIG. 11) are selected, mounted onto the introducer (FIG. 15) and threaded onto the shaft (10) in horizontal orientation (FIG. 16). The blade is placed as deep as it can go and then rotated into vertical orientation breaking the endplate and hooking into the vertebra (1) (FIG. 17). The blades alternate between clockwise and counterclockwise orientation. Variable size blades can be selected to better approximate the configuration of the disk space.

Figure 1:
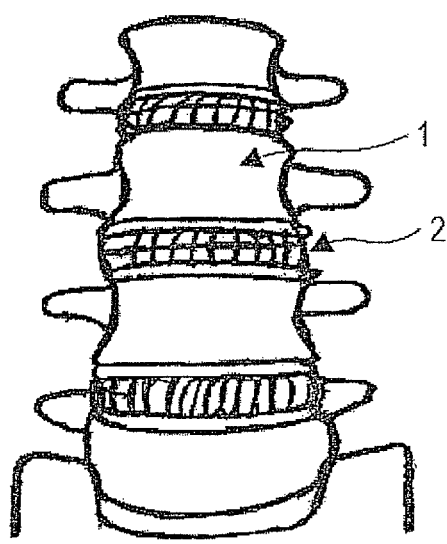
FIG. 1 illustrates an anterior view of the lumbar spine demonstrating vertebra (1) alternating with disk (2).
Figure 2:
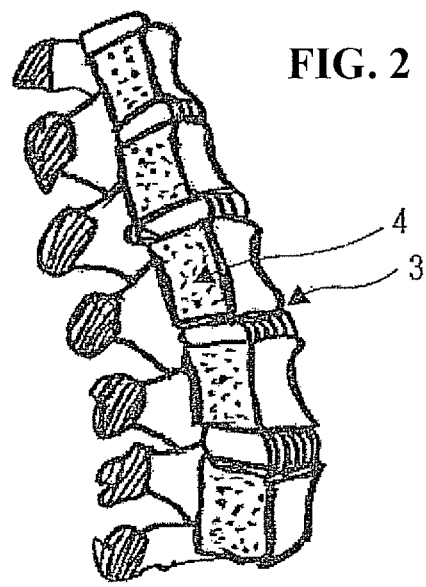
FIG. 2 illustrates an anterior view of the vertically sliced lumbar spine demonstrating internal composition of the vertebra with dense endplate (3) and softer inner part (4).
Figure 3:
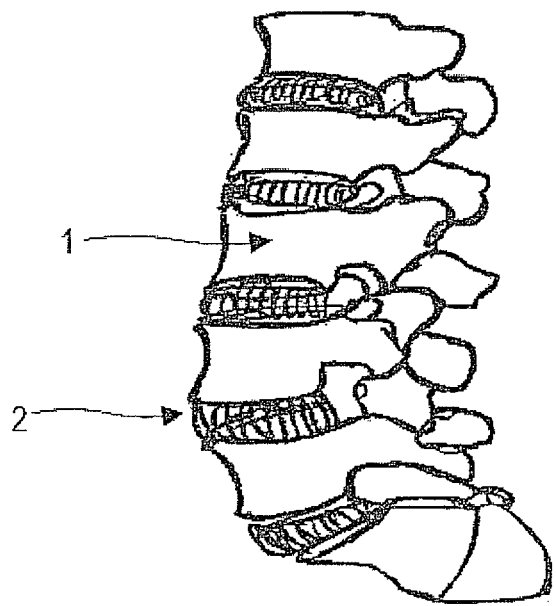
FIG. 3 illustrates a lateral (side) view of the vertebral column demonstrating normal curvature (lordosis) of the lumbar spine.
Figure 4:
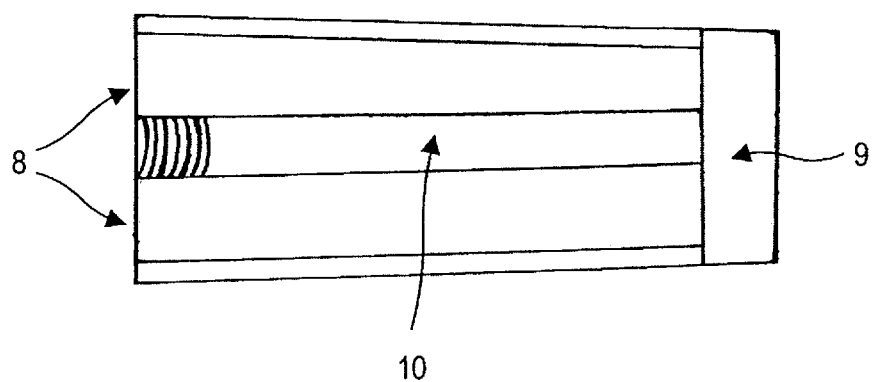
FIG. 4 illustrates a lateral (side) view of the preferred embodiment of a housing with front opening (8), back wall (9), and central shaft (10) fixed to the back wall (9).
Figure 5:
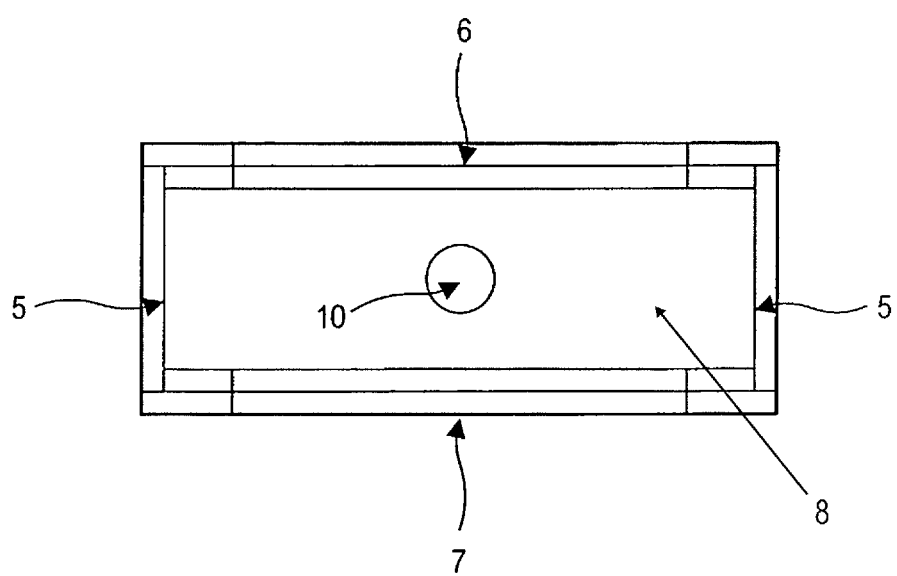
FIG. 5 illustrates an anterior (front) view through the front opening (8) of the housing with lateral weight bearing walls (5), top (6) and bottom (7) openings, and central shaft (10).
Figure 6:
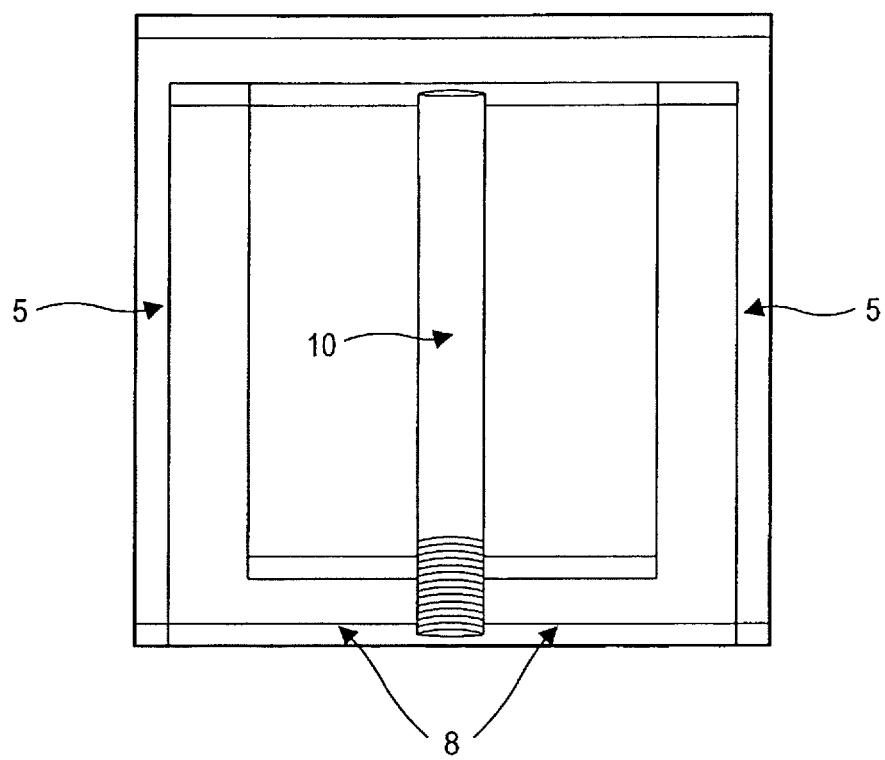
FIG. 6 illustrates a superior (top) view through the top opening (6) of the housing showing the central shaft (10).
Figure 7:
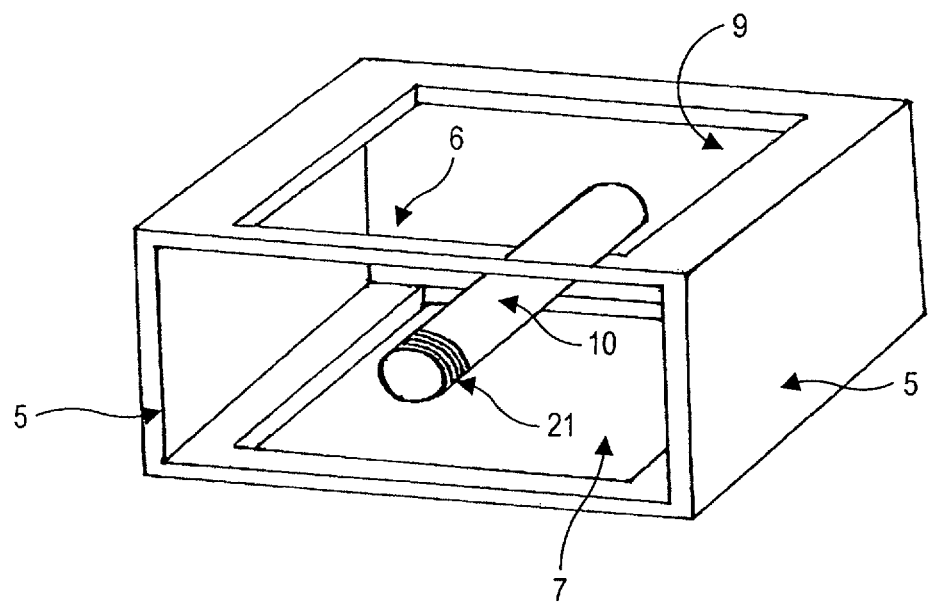
FIG. 7 illustrates a perspective view of the housing with lateral weight bearing walls (5), top (6) and bottom (7) openings, back wall (9), and a central shaft (10) including threaded end (21).
Figure 8:
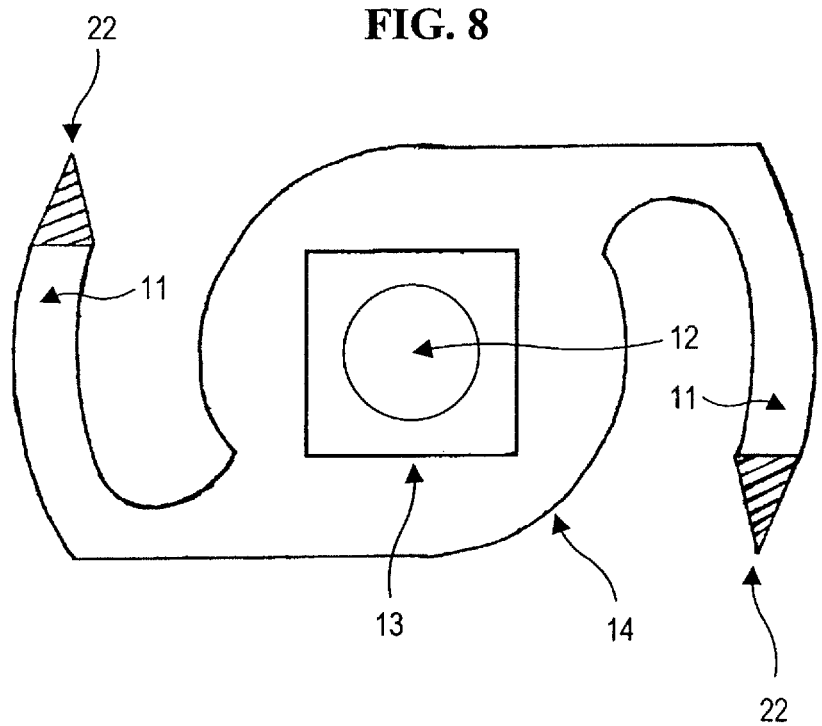
FIG. 8 illustrates a front view of the preferred embodiment of a clockwise blade (14) with cutting extensions (11) having sharp ends (22) that cut through the endplate (3) and into the cancellous bone (4) of vertebra (1). A central opening (12) fits over the shaft 10 of the housing. A control nut (13) is used to handle the blade and to thread the blade onto the shaft (10). A body of the blade (14) provides additional central weight bearing support against vertebral endplates.
Figure 9:
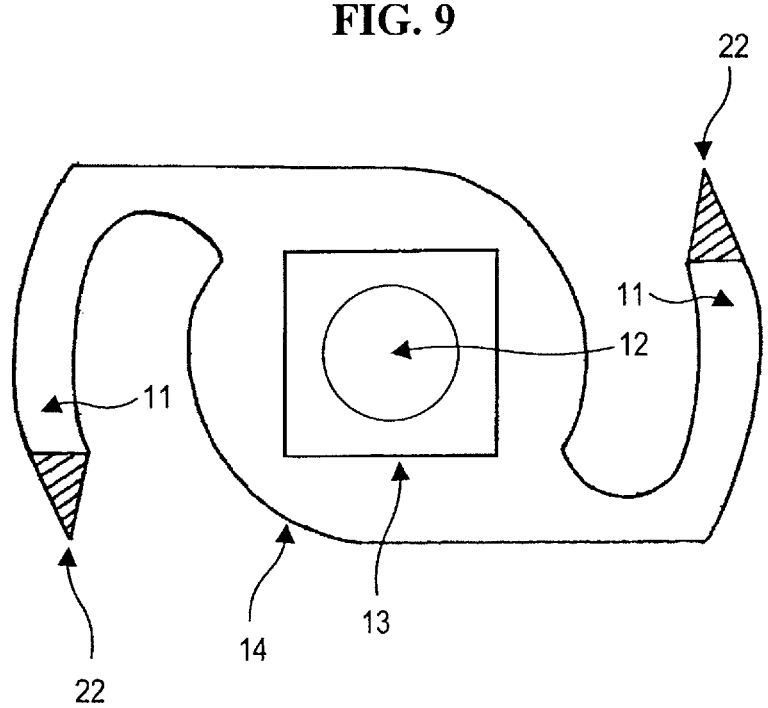
FIG. 9 illustrates a front view of the preferred embodiment of a counterclockwise clockwise blade (14).
Figure 10:
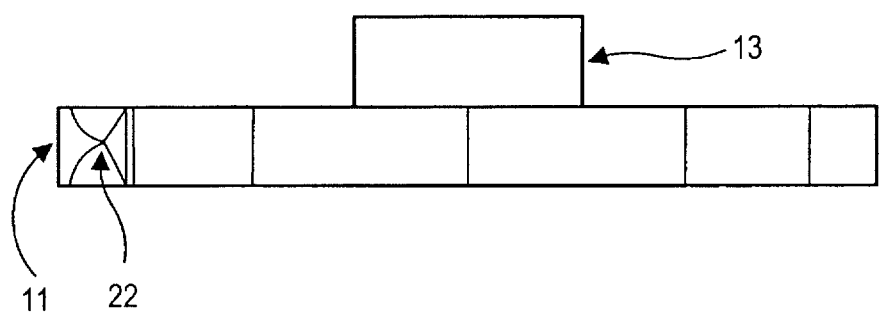
FIG. 10 illustrates a top view of the counterclockwise blade (14) showing cutting extension (11) having sharp end (22) and control nut (13).

Once all the blades are engaged, a tightening nut is threaded onto the end (21) of the shaft (10) of FIG. 7.

Figure 18:
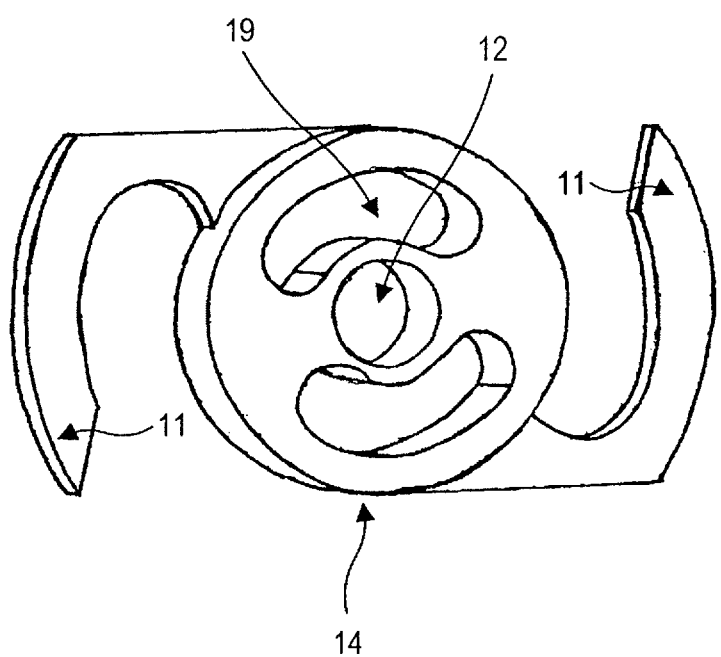
FIG. 18 illustrates an alternative embodiment of a blade (14) having central opening (12) and control openings (19) on opposing sides of the central opening (12) to rotate the blade (14) about the shaft (10). These blades (14) are preloaded into the housing prior to placement of the housing into the disk space (2).
Figure 19:
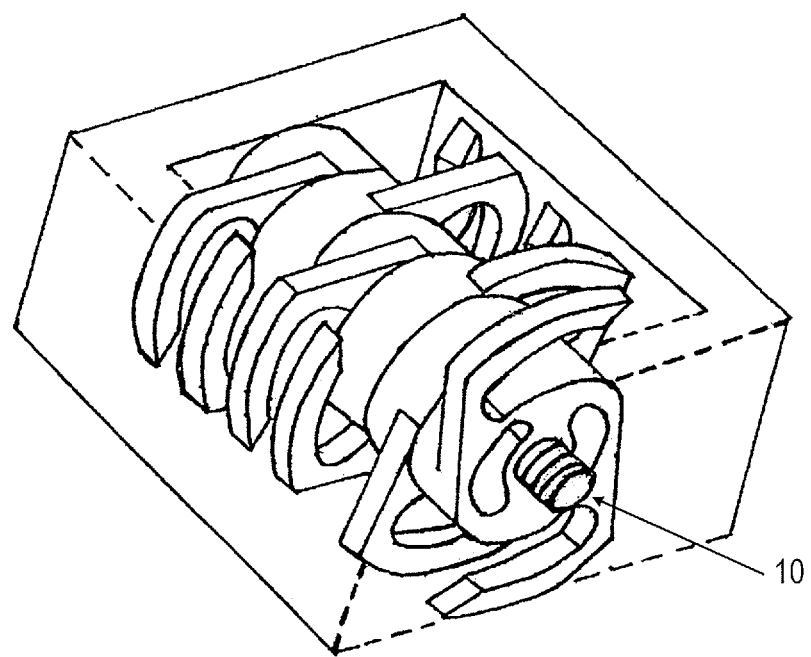
FIG. 19 illustrates a transparent housing and central shaft (10) with pre-loaded blades (14) showing front two blades rotated into final vertical position.
Figure 20:
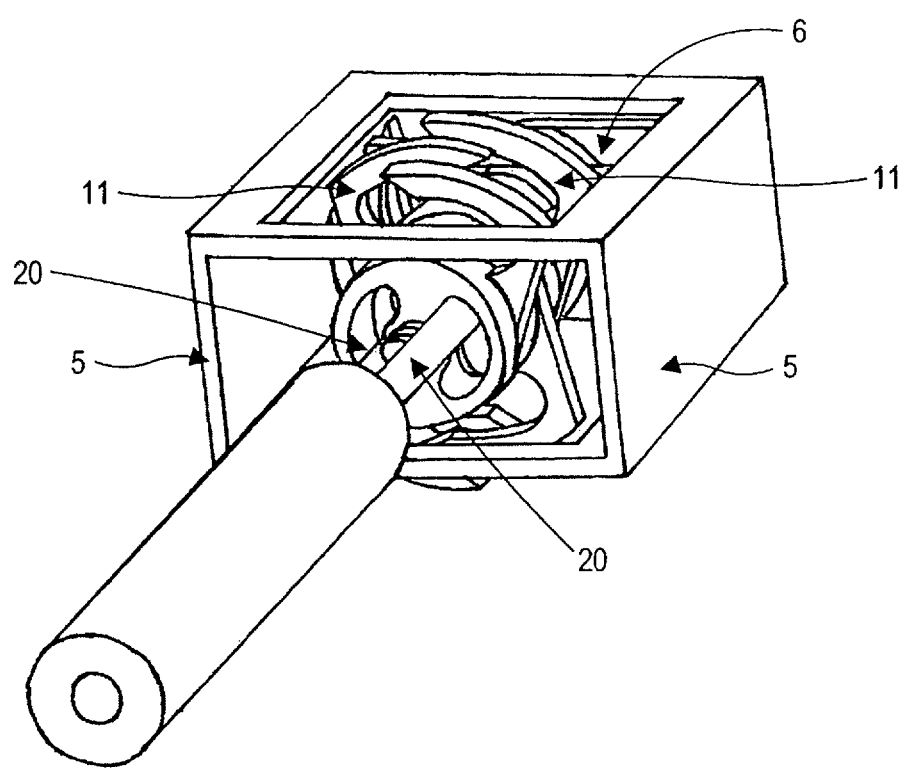
FIG. 20 illustrates a blade rotating tool that fits into control openings (19) of clockwise and counterclockwise blades (14) with prongs (20) of the rotating tool engaging and rotating the first three blades via the control openings (19).

In an alternative embodiment, alternating clockwise and counterclockwise blades (FIG. 18) are pre-loaded onto the shaft (10) and inside the housing (FIG. 19). The blades include a central opening (12) and control openings (19) on opposing sides of the central opening (12) to rotate the blades about the shaft (10). With the help of a blade rotating tool with prongs (20) engaging the control openings (19) (FIG. 20), the blades are rotated sequentially going from superficial to deep.

In another embodiment the housing expands horizontally and contains two shafts, which separate from each other upon expansion of the housing. In the initial collapsed configuration, preloaded clockwise and counterclockwise blades threaded on different shafts imbricate between each other. After the housing is expanded, the blades are pulled apart.

In another embodiment, a body (14) of a blade is configured as an oval so that the disk space is expanded as a blade is rotated.

The invention claimed is:

1. A fixation device comprising:
   a housing with a leading surface and a trailing surface;
   first and second shafts running from the leading surface to the trailing surface of the housing;
   at least one first blade having at least one first cutting extension with a sharp leading edge extending from the first shaft in a first orientation about the first shaft; and
   at least one second blade having at least one second cutting extension with as sharp leading edge extending from the second shaft in a second orientation about the second shaft, the
   second orientation being opposite to the first orientation;
   wherein the at least one first blade is rotatable in a direction according to the first orientation and the at least one second blade is rotatable in an opposite direction according to the second orientation, such that the at least one first cutting extension of the at least one first blade and the at least one second cutting extension of the at least one second blade are enabled to break an endplate of a vertebra, hook into the vertebra, and rigidly secure the vertebra to the fixation device to prevent separation of the vertebra from the fixation device during spinal motion.

2. The device of claim 1, wherein the at least one first blade includes a first set of opposing cutting extensions with sharp leading edges that are enabled to break endplates of adjacent vertebrae, hook into the adjacent vertebrae, and rigidly secure the adjacent vertebrae in relation to each other and to the fixation device to prevent separation of the vertebrae from the fixation device during spinal motion.

3. The device of claim 2, wherein the at least one second blade includes a second set of opposing cutting extensions with sharp leading edges that are enabled to break the endplates of adjacent vertebrae, hook into the adjacent vertebrae, and rigidly secure the adjacent vertebrae in relation to each other and to the fixation device to prevent separation of the vertebrae from the fixation device during spinal motion.

4. The device of claim 1, wherein the at least one first blade is rotatable in a clockwise direction according to the first orientation, and the at least one second blade is rotatable in a counterclockwise direction according to the second orientation.

5. The device of claim 1, wherein the at least one first blade and the at least second blade are imbricated between each other.

6. The device of claim 1, wherein the at least one first blade and the at least second blade are rotatable individually or as a group.

7. The device of claim 1, wherein the at least one first blade and the at least second blade vary in size.

8. The device of claim 1, wherein the at least one first blade and the at least second blade include portions configured to expand a disk space between adjacent vertebrae.

9. The device of claim 8, wherein the portions are further configured to provide weight-bearing support to the adjacent vertebrae.

10. The device of claim 1, wherein first and second shafts serve as axis of rotation to the at least one first blade and the at least second blade.

11. The device of claim 1, wherein the first and second shafts are fixed in relation to each other, or move away from each other when the housing is expanded at least in part in vertical and horizontal directions.

12. The device of claim 1, wherein the first and second shafts run perpendicular to the leading surface of the housing.

13. The device of claim 1, wherein the housing has a configuration of a box, a cylinder, or another geometric shape, the configuration including a height of the deep surface that is smaller than a height of the trailing surface.

14. The device of claim 1, wherein the housing comprises at least one material selected from metal, plastic ceramic, graphite, coral, and human bone product.

15. The device of claim 1, wherein the housing is formed at least in part from a porous material.

16. The device of claim 1, wherein the housing is absorbable.

* * * * *